US006828458B2

(12) United States Patent
Sovak et al.

(10) Patent No.: US 6,828,458 B2
(45) Date of Patent: Dec. 7, 2004

(54) TOPICAL ANTIANDROGEN FOR HAIR LOSS AND OTHER HYPERANDROGENIC CONDITIONS

(75) Inventors: Milos Sovak, La Jolla, CA (US); Allen L. Seligson, San Marcos, CA (US); Brian Campion, San Diego, CA (US); Jason W. Brown, Leucadia, CA (US)

(73) Assignee: Biophysica, Inc., La Jolla, CA (US)

( * ) Notice: Subject to any disclaimer, the term of this patent is extended or adjusted under 35 U.S.C. 154(b) by 0 days.

(21) Appl. No.: 09/580,503

(22) Filed: May 25, 2000

(65) Prior Publication Data

US 2004/0014732 A1 Jan. 22, 2004

(51) Int. Cl.$^7$ .................. C07C 233/05; A61K 31/16
(52) U.S. Cl. ......................... 564/158; 514/616
(58) Field of Search ............................ 564/158; 514/616

(56) References Cited

U.S. PATENT DOCUMENTS

| | | | |
|---|---|---|---|
| 4,636,505 A | 1/1987 | Tucker | 514/256 |
| 4,880,839 A | 11/1989 | Tucker | 514/613 |
| 5,411,981 A | 5/1995 | Gaillard-Kelly et al. | 514/386 |
| 5,656,651 A | 8/1997 | Sovak et al. | 514/396 |
| 5,750,553 A | 5/1998 | Claussner et al. | 514/392 |
| 6,184,249 B1 * | 2/2001 | Sovak et al. | 514/520 |
| 6,472,415 B1 * | 10/2002 | Sovak et al. | 514/398 |

FOREIGN PATENT DOCUMENTS

| | | |
|---|---|---|
| EP | 0 100 172 | 8/1984 |
| WO | WO 97/00071 | 1/1997 |
| WO | WO 0037430 A | 6/2000 |

OTHER PUBLICATIONS

Tucker, H. et al.: Nonsteroidal antiandrogens. Synthesis and structure–activity relationships of 3–substituted derivatives of 2–hydroxypropionanilides. J. Med. Chem., 1988, vol. 31, pp. 954–959.
Tucker, H. et al.: Resolution of the nonsteroidal antiandrogen 4'–cyano–3–[(4–fluorophenyl) sulfonyl]–2–dydroxy–2–methyl–3'–(trifluoromethyl)–propionamide and the determination of the absolute configuration of the active enantiomer. J. Med. Chem., 1988, vol. 33, pp. 885–887.
Battmann et al., J. Steroid Biochem. Molec. Biol. (1994), 48:55–60.
Battmann et al., J. Steroid Biochem. Molec. Biol. (1998), 64:103–111.
Brouwer et al., J. of Dermatology (1997), 137:699–702.
Cousty–Berlin, J. Steroid Biochem. Molec. Biol. (1994), 51:47–55.
Kaufman, Dermatologic Clinics (1996), 14:697–711.
Kondo et al., Prostate (1996), 29:146–52.
Kuil and Brinkmann, Eur. Urol. (1996), 29:78–82.
Shapiro and Price, Dermatologic Clinics (1998), 16:341–56.
Simard et al., Urology (1997), 49:580–9.
Toney et al., J. Steroid Biochem. Molec. Biol. (1997), 60:131–6.

* cited by examiner

Primary Examiner—Shailendra Kumar
(74) Attorney, Agent, or Firm—Fliesler & Meyer LLP

(57) ABSTRACT

Compound (2-hydroxy-2-methyl-N-(4-X-3-(trifluoromethyl)phenyl)-3-(2,2,2-perfluoroacylamino) propionamide) applied topically, specifically inhibits and/or eliminates cutaneous androgen receptors and thus finds cosmetic use in skin afflictions associated with excess androgens such as hair effluvium, hirsutism, acne and androgenic alopecia.

20 Claims, No Drawings

TOPICAL ANTIANDROGEN FOR HAIR LOSS AND OTHER HYPERANDROGENIC CONDITIONS

TECHNICAL FIELD

The field of this invention is methods and compositions for suppressing androgen receptors, particularly cutaneous androgen receptors, for the treatment of androgenic hair effluvium and alopecia.

BACKGROUND

The pathophysiology of both male and female hair loss is not yet understood. Factors ranging from low scalp blood flow, deficiency of nutrients and hair-related vitamins, microbially-driven inflammatory changes and the like have been considered. It is, nevertheless, apparent that one of the most influential factors is androgenic hormones acting on hair follicles in the scalp. Androgenic hormones promote growth of the beard and of body hair throughout life. The growth of scalp hair also depends on androgenic hormones, but only in early life. With increasing age, androgenic hormones switch from promoting growth of scalp hair to promoting its loss, known as androgenic effluvium and alopecia. In hirsutism and acne vulgaris, an excess of cutaneous androgenic hormones was shown to be the major factor in those complex syndromes.

The androgenic hormones act via androgenic receptors, a cellular protein transcription factor which interacts with a specific region of DNA. Testosterone and its much more potent analog 5-alpha-dihydrotestosterone (DHT) must bind to androgenic receptors first to become active. Scalp androgenic hormones are derived either from the systemic circulation and/or synthesized in the skin and have been shown to bind to androgenic receptors located in the hair follicles.

Systemic antiandrogens, steroidal or nonsteroidal, are compounds which generally are administered orally. Developed to block androgenic hormones from binding to androgenic receptors, they are used primarily for the treatment of prostate cancer and of certain systemic hyperandrogenic conditions. Systemic antiandrogens are stable in vivo and block all androgenic receptors indiscriminately, thus inducing a number of side effects such as loss of libido and of male sexual functions. Skin disorders in otherwise healthy males thus cannot be treated by systemic antiandrogens given orally, nor can they be given topically, since those that are currently in use are absorbed from the skin.

The use of systemic antiandrogens such as the steroids cyproterone acetate, chlormadinone acetate and spironolactone was proposed for treatment of women suffering from androgenic effluvium and alopecia but concerns for side effects call for clinical studies (Diamanti-Kandarakis, *Current Pharm Des,* 1999 September, 5(9): 707–23). There are other limitations: It is known that at least in males chronically treated with systemic antiandrogens, the resulting extended androgenic receptor blockade leads to mutation of the androgen receptors, and that the mutated receptors attain the capability of being activated by other substances such as various steroidal metabolites, progestins and estrogens, insulin-like growth factor, epidermal growth factor and keratinocyte growth factor and neuroendocrine transmitters such as serotonin. It has also been shown that the androgenic receptor blockade amplifies synthesis of the androgenic receptor gene. It is apparent therefore that therapy of hyperandrogenic skin afflictions in women using currently available systemic antiandrogens is not ideal and that in men it would not be acceptable at all.

For the treatment of androgenic effluvium and alopecia, the state of therapeutic art is the topical Minoxidil (an antihypertensive drug) and its derivatives, such as aminexil. Minoxidil has been observed to arrest male hair loss, and to an extent, promote regrowth, but only in the vertex scalp; the activity is tentatively explained among others as activation of prostaglandin endoperoxide synthase-1, increase of local blood flow, suppression of bacterial infection and/or a modification of androgenic hormone metabolism in the dermal papilla. (Michelet, et al. *Journal of Investigative Dermatology,* 1997 February, 108(2): 205–9; Pirard-Franchimont, et al. *Dermatology,* 1998; 196 (4): 474–7; Sato, et al. *Journal of Dermatological Science,* 1999 February 19(2): 123–5).

Finasteride (Scow, et al. *American Family Physician,* 1999 April 15, 59(8): 2189–94, 2196) has also been used for the treatment of androgenic effluvium and alopecia. Taken orally and daily, it suppresses systemic conversion of testosterone to dihydrotestosterone (DHT), thus reducing overall androgen activity, including in the scalp. The studies indicate that about half of the men treated achieved slight to moderate improvement of effluvium in the anterior mid scalp and in approximately one-half, the effluvium was arrested. Various side effects including loss of libido and of erectile function were reported which disappeared after drug withdrawal. (Kaufman, et al. *Journal of the American Academy of Dermatology.* 1998 October, 39 (4 Pt. 1): 578–89). No studies however are yet available which prove unequivocally that a long term systemic manipulation of hormonal balance with finasteride is harmless.

Popular traditional Chinese medicine utilized topical treatment of androgenic effluvium and alopecia with an extract from *Polygonum cuspidatum,* an asian cane which contains resveratrol. Phytoestrogens and other substances are known to interfere with androgenic receptors. (Mitchell, et al. *Cancer Res.* (1999) 58:5892–5.

It therefore would be of interest to develop an antiandrogen which would suppress or eliminate rather than only block androgenic receptors in a defined topical location, and which would not be irritating or resorbable from the skin. Such a compound would be useful in the therapy of androgenic hormones-dependent cutaneous afflictions.

Relevant Literature

A patent application has been filed for antiandrogens, whose activity was found, rather than blocking, suppressed or even eliminated the androgen receptor in a concentration and time dependent fashion. (Sovak, M. S.; Bressi, J. C.; Douglas, J.; Campion, B.; Wrasidlo, W. Androgenic Directed Compositions, U.S. application Ser. No. 09/215, 351, 1998)

U.S. Pat. No. 5,656,651 and WO97/00071, and references cited therein, describe anti-androgenic directed compositions based on phenyldimethylhydantoins, where the phenyl group is substituted with a trifluoromethyl group and either a cyano or nitro group. See also, Battmann et al., *J. Steroid Biochem. Molec. Biol.* 64:103–111 (1998); Cousty-Berlin, ibid 51:47–55 (1994); and Battmann et al., ibid 48:55–60 (1994), for a description of analogous compounds and their activity. For other compounds having the substituted phenyl moiety, see U.S. Pat. Nos. 4,636,505 and 4,880,839, and EP 0 100 172. For discussions about the activities of androgens, see Kuil and Brinkmann, *Eur. Urol.* 29:78–82 (1996); Kondo et al., *Prostate* 29:146–152 (1996), and Simard, et al., *Urology* 49:580–589 (1997). For discussions about alopecia and its relationship with androgens, see Kaufman, *Dermatologic Clinics* 14:697–711 (1996); Toney et al., *J. Steroid Biochem. Molec. Biol.* 60:131–136 (1997); Brouwer et al., *J. of Dermatology* 137:699–702 (1997); and Shapiro and Price *Dermatologic Clinics* 16341–356 (1998).

SUMMARY OF THE INVENTION

Novel compounds are provided that are 2-hydroxy-3-perfluoroacylamidopropionanilides, where the phenyl is substituted. The compounds inhibit or eliminate skin androgenic receptors without being systemically resorbed and thus find use as a topical cosmetic in a treatment of hair effluvium, alopecia and other skin afflictions dependent on an excess of androgen hormones. The compounds are applied as conventional topical formulations in an amount to reduce the level of androgenic receptors.

DESCRIPTION OF THE SPECIFIC EMBODIMENTS

The subject compounds are N-(4-X-3-(trifluoromethyl)phenyl)2-hydroxy-2-methyl-3-(perfluoroacylamino) propionamides, where X is nitro, cyano or halogen of atomic number 9–35, particularly chlorine and the perfluoroacyl group is of from 2 to 3 carbon atoms and 0–1 hydrogen atom. Perferably X is nitro and the perfluoroacyl group has 0 hydrogen atoms.

The compounds may or may not have one or more stereoisomeric centers and may be used as racemic mixtures or be resolved into their enantiomers and used as enantiomers.

Of particular interest are the following compounds.

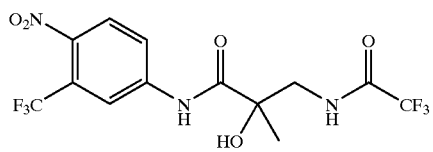

BP-766

2-hydroxy-2-methyl-N-(4-nitro-3-(trifluoromethyl)phenyl)-3-(2,2,2-trifluoroacetylamino)propionamide

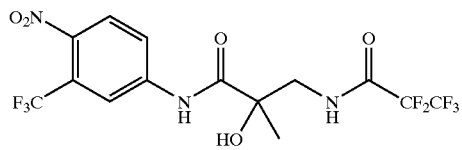

BP-780

2,2,3,3,3-pentafluoro-N-(2-hydroxy-2-(N-(4-nitro-3-(trifluoromethyl)phenyl)carbamoyl)propyl)propionamide.

The subject compounds can be used as safe topical antiandrogens, for treatment of cutaneous diseases characterized by excess of androgens such as hirsutism, acne and hair effluvium or androgenic alopecia. The subject compounds display one or more of the following properties: specific binding and high affinity to the androgen receptor; suppressing synthesis of and/or eliminating the androgen receptor in a concentration dependent fashion; no detectable systemic resorption when applied topically; and rapid biodegradability into components of low toxicity and no androgenic activity. The subject compounds may be used individually or in combination and with other antiandrogens such as cyproterone acetate, flutamide, bicalutamide and nilutamide or other treatments for such as Finasteride or topical compounds such as Minoxidil or Aminexil, where reduced amounts of the other compounds may reduce side effects, while enhancing the activity of the subject compounds for their intended indication.

Of particular interest is to employ a regimen where the subject compound is used with an agent commonly used for treating hair effluvium and/or alopecia, such as finasteride, minoxidil² or Aminexil® (a trademark of Oreal), where the dosage employed for the known agent may be the same, usually lower, as in the absence of the subject. Determining the optimum dosage for the combination can be done in conventional ways using appropriate clinical studies and varying ratios of the two ingredients, which may be in a common formulation or employed as two independent formulations.

Various plant extracts which are useful in treating alopecia and decoctions such as birch extract, nettle extract, green tea extract, or the like, as may be conventionally employed and as may be moderated for use in conjunction with the subject compounds. The treatments may be performed concurrently, consecutively or in accordance with a predetermined regimen of particular interest is the use of resveratrol, a plant extract which can be obtained by extraction from plants such as Asian cane. Synthetic reservation is available from Aldrich. The plant extracts may be used in accordance with conventional applications, preferably at reduced dosage or frequency of administration.

Therapeutic compositions can be formulated in accordance with conventional ways and the indication to be treated. A predetermined regimen is employed, usually involving daily application one or more times until no further improvement is observed, which may take weeks or months. The composition may be formulated for topical use, as an alcohol, aqueous or oily solution, lotion or dispersion, or the like. Conventional carriers include vegetable oils, vaseline, lanolin, ethanol, isopropanol, etc. Excipients, stabilizers, and additives such as plant extracts and vitamins or the like may be employed. The concentration may be from about 0.1 to 10 by weight %. A preferred formulation is prepared as a 2% by weight solution in anhydrous isopropanol, although other alcohols would function as well. The individual dosage is in the range of about 0.1 mg to about 5 g, usually not more than about 200 mg/dose, more usually 10 to 100 mg/dose, where one may apply the formulation one or more times, generally from about 1 to 3 times daily, with a daily dose in the range of about 10–200 mg/day, more usually about 20 to 100 mg/day. Generally the formulation is rubbed into the roots of the hair, or affected skin in a total volume of about 1 ml. Frequent washing of the hair should be avoided, and soaps rather than detergent-based shampoos are preferably used for washing the hair. Treatment should be continued for as long as a curative effect is desired; upon cessation of therapy, androgen receptors are again synthesized.

The subject compounds may be used in competitive assays or as controls for evaluating other compounds as to their capability to affect the androgen receptor. Thus, specific cell lines may be employed where the effect of an agent on the activity of a subject compound may be determined in relation to the survival rate or other indicia of the target cells. By providing cells producing androgen receptors, where the androgen receptor production is naturally occurring or enhanced due to genetic-modification of the cells, one may perform assays for effectiveness of candidate drugs, using the subject compounds as controls.

The following examples are offered by way of illustration and not by way of limitation.

EXAMPLES

Example 1

4-nitro-3-trifluoromethyl-N-(2-hydroxy-2-methyl-3-amino (BP-34)

A pressure reactor was charged with 4-nitro-3-trifluoromethyl-N-[2,3-epoxy-2-methyl propionyl]aniline (prepared according to EPA 100, 172)(10.0 g, 34.46 mmol)

and methanol (100 ml). After cooling to −70° C., ammonia in excess was condensed into the reactor which was sealed and stirred for 14 hours. Following evaporation, the crude solid was washed w3ith cold dichloromethane and (50 ml). Filtration and drying gave 6.1 gPG-34 (58% yield). Melting point: 142–145° C.

Example 2

2-hydroxy-2-methyl-N-(4-nitro-3-(trifluoromethyl) phenyl)-3-(2,2,2-trifluoroacetylamino)propanamide BP-34 (500 g, 1.63 mol), ethyl acetate (2.0 L) and triethylamine (295 ml, 2.12 mol). were stirred at 5° C. Trifluoroacetic anhydride (299 ml, 2.12 mol) was added, stirred for 30 min, washed with 1N HCl (1.0 L), saturated aqueous bicarbonate (2×2.0 L) and brine (1.0 L). After treatment with $MgSO_4$, the organic layer was evaporated, and the residue purified to yield 562 g, (86%).

$^1$H NMR (DMSO-$d_6$, 500 MHz): $\delta$10.56 ($s_1$ ArONHC (O)); $\delta$9.31 $t_2$ NHC(O)$CF_3$). $^{19}$F NMR (DMSO-$d_6$, 470 MHz): $\delta$-58.4 (s1 Ar$CF_3$); $\delta$-73.4 (s1 C(O)$CF_3$). Mass spec (m/z): 426 (M+$Na^+$).

Example 3

Effects of BP-766 on the Androgen Receptor

The interaction of BP-766 with androgenic receptors was studied by incubation with LNCaP cells, (known to contain human AR), subsequent cell lysis and the Western Blot assay to identify and quantify the androgenic receptors protein. Table 1, below, shows average percent of remaining androgenic receptors contained in the lysate following 16, 24, and 48 hour incubation of the cells with BP-766, its byproduct of biodegradation, BP-34, and of the two standard systemic antiandrogens, bicalutamide and hydroxyflutamide, all run in duplicate.

TABLE 1

Percent Androgen Receptor Remaining in LNCaP Cells after incubation with other antiandrogens[1] and/or a degradation product of BP-766

| Compound: | @ 3$\mu$ Molar conc.: | @ 10$\mu$ Molar conc.: |
|---|---|---|
| BP-766 16 hrs. incubation | 47 | 9 |
| BP-766 24 hrs. incubation | 51 | 7.3 |
| BP-766 48 hrs. incubation | 59 | 4.1 |
| BP-34 48 hrs. incub. | 97 | 98 |
| Bicalutamide[2], 48 incub. | 97 | 89 |
| Hydroxyflutamide, 48 hrs. incub. | 98 | 94 |

[1]Resveratrol in this assay had a neglibible effect on AR, at 10 $\mu$M conc. About 46% AR remained. When cells were incubated together with 3 $\mu$M Resveratrol/BP-766, (1:1), the combined effect was about twice as great as with BP-766 alone, after 16 hrs incubation, suggesting synergy of such combination.
[2]AstraZeneca.

The systemic antiandrogens hydroxyflutamide and bicalutamide, did not a affect the androgenic receptors significantly at any concentration after 48 hrs., while BP-776 suppressed androgenic receptors at 3 $\mu$M concentration within 16 hrs. and practically eliminated the androgenic receptors at 10 $\mu$M concentration by 48 hours. BP-34, the aromatic product of degradation of BP-766, had no effect on the androgenic receptors.

Example 4

Cutaneous Absorption and Irritation Studies In Rabbits

BP-766 was applied topically twice daily to simulate the intended human application (0.6 mg/kg-day), on the two 10 $cm^2$ separate areas of a closely shaved skin of four rabbits, for ten days. One ml blood samples were collected at 2, 5 and 21 hours after the first application, and once every other day thereafter. Serum was analyzed by HPLC. Using spiked and blank serum samples and a linearity determination, the limits of detection of BP-766 and/or BP-34 were established as approximately 10 ng/ml. No BP-766 or BP-34 was found in any of the samples. The cutaneous absorption in rabbits is known to be about 5 to 6 times greater than in humans (Marzulic, F. N. and Maibach, H.: *Dermatotoxicology*, 5$^{th}$ Edition, Taylor & Frasier, Washington, D.C. 1966) so that even with the detection limits of this method, only trace amounts could ever be expected in humans. The rabbits were also observed daily for signs of cutaneous irritation: none was detected over the entire course of the experiment.

Example 5

Skin Irritation Potential of BP-766

BP-766 was also evaluated by an independent laboratory according to ISO 10 993-10, in rabbits. A single application of 0.5 ml as a 1% (m/v) solution in anhydrous isopropyl alcohol and/or the vehicle only was employed. The application site was covered in one group, and not covered in an other group, each consisting of six rabbits. The skin surface was observed at 24, 48 and 72 hours after application. Non-irritability was defined by an arbitrary index, ranging from 0 to 0.4. The values obtained for BP-766 and/or the vehicle ranged from 0.08–0.14, which indicates that no skin irritation potential was found.

Example 6

Biodegradability of BP-766 in Human Serum

BP-766 was tested for degradation by incubation with human serum at 38° C., at a concentration of 0.5 mg/ml. The amount of intact compound, determined by HPLC in serum at different time-points, is reported in Table 2. It would be desirable for safety that should BP-766 for any unexpected reason be resorbed from the skin, it should decompose into rapidly excretable non-toxic components. The only products of biodegradation of BP-766 are the precursor BP-34, and trifluoroacetic acid, which both have good biological tolerance. Thus, trifluoroacetic acid showed no toxicity when fed to mice. (Permadi, H; Lundgren, B; Andersson K; Sundberg C; DePierre J W. Effects of perfluoro fatty acids on peroxisome proliferation and mitochondrialsize in mouse liver: dose and time factors and effect of chain length. *Xenobiotica*, (1993) Vol 23, No. 7, pp. 761–70). Orientational toxicity of BP-34 is described further below.

TABLE 2

Biodegradation of BP-766 in Human Serum:

| Time (hours) | % BP-766 remaining in human serum (38° C.) |
|---|---|
| 0 | 100 |
| 6 | 54.3 |
| 24 | 10.9 |
| 48 | Traces |

Example 7

Evaluation of Systemic Toxicity of BP-766 and of its Degradation Product BP-34

The systemic toxicity of BP-766 was orientationally evaluated by multiple intraperitoneal (i.p.) injections in mice. BP-766 was injected daily for seven days each time at a dose of 300 to 500 mg/kg . The LD50 (daily dose for seven days that resulted in 50% mortality) of BP-766 was estimated at 450 mg/kg bw. The murine maximum tolerated dose (MTD) was approximately 300 mg/kg. For BP-34, i.p. injections of 100–300 mg/kg produce no mortalities in mice. Morbidity, but not mortality, was observed at 300 mg/kg. The murine MTD of BP-34 was found to be approximately 250 mg/kg.

Example 8

Evaluation of Acute Oral Toxicity in Mice and Rats

Acute oral toxicity of BP-766 was determined in NMRI mice and Wistar rats. The LD50 was calculated by probit analysis, with 5 mice or rats at each dose level (1500, 2000, and 2500 mg/kg) tested.

The LD50 of BP-766 in male and/or female mice was calculated as 2871.7 mg/kg and 2232.0 mg/kg, respectively. The LD50 of BP-766 in male and/or female rats could not be determined since only one male rat died (at the 1500 mg/kg ), and none of the female rats did. Therefore, the LD50 of BP-766 in rats is greater than 2500 mg/kg body weight.

Example 9

Evaluation of Shelf-Stability of Formulated BP-766

In an accelerated stability study, formulated solutions of BP-766 in 97% isopropanol or ethanol:water (60:40), and incubated at 55° C. or room temperature, showed but a small change, by HPLC, for up to six days. (Table 3). The data shown in Table 4 suggest that BP-766 in anhydrous isopropanol should be stable at least for five years at room temperature (20° C.). (Connors, Kenneth A; Amidon, Gordon L.; Stella, Valentino J. *Chemical Stability of Pharmaceuticals—A Handbook for Pharmacists.* Second Edition, 1986, John Wiley & Sons)

TABLE 3

Accelerated Shelf Stability of BP-766 in aqueous alcohols.

| Time (hours) | % BP-766 Isopropanol (3–5% water) (55° C.) | % BP-766 60/40 EtOH/H$_2$O (RT) | % BP-766 60/40 EtOH/H$_2$O (55° C.) |
|---|---|---|---|
| 0 | 100 | 100 | 100 |
| 6 | 99.6 | — | — |
| 24 | 99.1 | 99.9 | 99.1 |
| 48 | — | 99.69 | 98.2 |
| 144 | 98.7 | — | — |

TABLE 4

Accelerated Shelf Stability of BP-766 in anhydrous isopropanol.

| Time (weeks) | 0 | 1 | 2 | 3 | 4 | 5 | 6 | 7 | 8 |
|---|---|---|---|---|---|---|---|---|---|
| BP-766 remaining | 100 | 99.6 | 99.4 | 99.3 | 99.2 | 98.9 | 98.8 | 98.3 | 98.4 |

Example 10

BP-766 in the Treatment of Androgenic Hair Effluvium and Alopecia

In six volunteers with incipient androgenic effluvium and/or or alopecia, BP-766 was applied on the scalp(behind the hair-thinning line) as a 2% solution in anhydrous isopropanol, 1 ml, twice daily (0.6 mg/kg) for a period of 8 weeks; no dermal irritation was in any of the volunteers. BP-766 arrested the effluvium of the frontal hairline in all six volunteers after 2 weeks. After 4 months use, by two volunteers, an evident regrowth was observed. Four volunteers also employed Minoxidil as an admixture, in a 2% concentration, with similar results.

Example 11

2,2,3,3,3-pentafluoro-N-(2-hydroxy-(n-(4-nitro-3-(trifluoromethyl)phenyl)carbanoyl)propyl) propanamide. (BP-780)

BP-34 (35.4 g, 0.115 mol), tetrahydrofuran (140 ml), and triethylamine (17.7 ml, 0.127 mol) were stirred at 5° C. Pentafluoropropionic anhydride (39.3 g, 0.127 mol) was added and stirred for 2 hours at room temperature. After solvent removal, the product was dissolved in ethyl acetate (250 ml) and washed with H2O (250 ml) and 0.1 N Hcl (250 ml) After treatment with MgSO4, the solvent was evaporated and the residue crystallized from ethyl acetate.. (50% yield).

$^1$H NMR (CD3 CN, 500 MHz): $\delta$9.50 (s1 ArONHC(O)); $\delta$7.78 t, NHC (O)CF$_2$CF$_3$). $^{19}$FNMR(CD3 CN, 470 MHZ): $\delta$–59.7 (s$_1$ArCF$_3$); 67 –82.8; $\delta$–122.45 (d C(O)CF$_2$). Mass spec (M/Z): 476(MNa$^+$).

This novel suppressor of cutaneous androgen receptors described herein offers a sound therapeutic concept for treatment of androgenic effluvium and alopecia, applicable to both males and females. Although the foregoing invention has been described in some detail by way of illustration and examples for purposes of clarity of understanding, it will be obvious that certain changes and modifications may be practiced within the scope of the appended claims. All references cited herein are incorporated herein by reference, as if set forth in their entirety.

What is claimed is:

1. A compound of the formula 2-hydroxy-2-methyl-N-(4-X-3-(trifluoromethyl)phenyl)-3-(perfluoroacylamino) propionamide), wherein X is nitro, cyano or halo of atomic number 9–35, and perfluoroacylamido is from 2–3 carbon atoms and of from 0–1 hydrogen atom.

2. A compound according to claim 1 of the formula 2-hydroxy-2-methyl-N-(4-nitro-3-(trifluoromethyl)phenyl)-3-(pefluoroacetylamino)propionaide).

3. A compound according to claim 1 of the formula 2-hydroxy-2-methyl-N-(4-nitro-3-(trifluoromethyl)phenyl)-3-(perfluoropropionylamino)propionamide.

4. A method for treating symptoms of at least one of androgenic effluvium and alopecia in a host, said method comprising:
   topically administering to said host a therapeutically effective amount for the treatment of said androgenic effluvium or alopecia of a composition comprising a compound according to claim 1,
   for a time sufficient to treat said androgenic effluvium or alopecia.

5. A method according to claim 4, wherein said topically administering further comprises treatment with a second antiandrogenic agent for the treatment of androgenic effluvium or alopcecia.

6. The method according to claim 4, wherein said therapeutically effective amount is at a daily dosage in the range of about 10–200 mg/day.

7. A method of treating symptoms of a cutaneous affliction dependent upon the suppression or elimination of androgen receptor in a host, said method comprising:
   topically administering to said host in a predetermined regimen an effective amount of a composition comprising a compound according to claim 1 to treat said cutaneous affliction.

8. The method according to claim 7, wherein said cutaneous affliction is a hyperandrogenic skin syndrome.

9. A cosmetic or pharmaceutical formulation comprising a compound according to claim 1 in an amount of at least about 0.1% and a pharmacologically and/or cosmetically acceptable carrier.

10. A method for decreasing synthesis of cutaneous androgen receptors in a cell, said method comprising:

contacting said cell comprising said cutaneous androgen receptors with a compound according to claim 1 in an amount sufficient to decrease synthesis of said cutaneous androgen receptors.

11. The method according to claim 10, wherein said cell is a follicle cell.

12. The method of claim 4, wherein said method comprises:

topically administering to said host a therapeutically effective amount for the treatment of said androgenic effluvium or alopecia of a composition comprising a compound of the formula 2-hydroxy-2-methyl-N-(4-nitro-3-(trifluoromethyl)phenyl)-3 (perfluoroacotylamino)propionamide) sufficient to treat said androgenic effluvium or alopecia.

13. The method of claim 4, wherein said method comprises topically administering to said host a therapeutically effective amount for the treatment of said androgenic effluvium or alopecia of a composition comprising a compound of the formula 2-hydroxy-2-methyl-N-(4-nitro-3-(trifluoromethyl)phenyl)-3-(perfluoropropionylamino)propionamide sufficient to treat said androgenic effluvium or alopecia.

14. The method of claim 7, wherein said method comprises:

topically administering to said host in a predetermined regimen an effective amount of a composition comprising a compound of the formula 2-hydroxy-2-methyl-N-(4-nitro-3-(trifluoromethyl)phenyl)-3-(perfluoroacetylamino)propionamide) to treat said cutaneous affliction.

15. The method of claim 7, wherein said method comprises:

topically administering to said host in a predetermined regimen an effective amount of a composition comprising a compound of the formula 2-hydroxy-2-methyl-N-(4-nitro-3-(trifluoromethyl)phenyl)-3-(perfluoropropionylamino)propionamide to treat said cutaneous affliction.

16. The method of claim 10, said method further comprising:

contacting said cell comprising said cutaneous androgen receptors with a compound of the formula 2-hydroxy-2-methyl-N-(4-nitro-3-(trifluoromethyl)phenyl)-3-(perfluoroacetylamino)propionamide) in an amount sufficient to decrease synthesis of said cutaneous androgen receptors.

17. The method of claim 10, said method further comprising: contacting said comprising said cutaneous androgen receptors with a compound of the formula 2-hydroxy-2-methyl-(4nitro-3-(trifluoromethyl)phenyl)-3-(perfluorapropionylamino)propionamide in an amount sufficient to decrease synthesis of said cutaneous androgen receptors.

18. The method according to claim 4, wherein said therapeutically effective amount is at a daily dosage in the range of about 0.1 mg to about 5 g per day.

19. The method of claim 4, further comprising administering an extract of *Polygonum cuspidatum*.

20. The method of claim 19, wherein said extract comprises at least one of reservation and a glycon of resveratrol.

* * * * *